US012595517B2

(12) United States Patent
Cartron et al.

(10) Patent No.: US 12,595,517 B2
(45) Date of Patent: Apr. 7, 2026

(54) METHOD TO TREAT AND STRATIFY A PATIENT SUFFERING FROM A CANCER

(71) Applicants: INSERM (INSTITUT NATIONAL DE LA SANTÉ ET DE LA RECHERCHE MÉDICALE), Paris (FR); INSTITUT DE CANCÉROLOGIE DE L'OUEST, Angers (FR); NANTES UNIVERSITÉ, Nantes (FR)

(72) Inventors: Pierre-François Cartron, Nantes Cedex 1 (FR); Gwenola Bougras-Cartron, Nantes Cedex 1 (FR)

(73) Assignees: INSERM (INSTITUTE NATIONAL DE LA SANTE ET DE LA RECHERCHE MEDICALE), Paris (FR); INSTITUTE DE CANCÉROLOGIE DE L'OUEST, Angers (FR); NANTES UNIVERSITÉ, Nantes (FR)

( * ) Notice: Subject to any disclaimer, the term of this patent is extended or adjusted under 35 U.S.C. 154(b) by 452 days.

(21) Appl. No.: 18/245,067

(22) PCT Filed: Sep. 13, 2021

(86) PCT No.: PCT/EP2021/075132
§ 371 (c)(1),
(2) Date: Mar. 13, 2023

(87) PCT Pub. No.: WO2022/053691
PCT Pub. Date: Mar. 17, 2022

(65) Prior Publication Data
US 2023/0357860 A1     Nov. 9, 2023

(30) Foreign Application Priority Data
Sep. 14, 2020    (EP) .................................... 20306025

(51) Int. Cl.
| C12Q 1/6886 | (2018.01) |
| A61K 31/496 | (2006.01) |
| A61P 35/00 | (2006.01) |

(52) U.S. Cl.
CPC .......... *C12Q 1/6886* (2013.01); *A61K 31/496* (2013.01); *A61P 35/00* (2018.01); *C12Q 2600/106* (2013.01); *C12Q 2600/158* (2013.01); *C12Q 2600/178* (2013.01)

(58) Field of Classification Search
CPC ............ C12Q 1/6886; C12Q 2600/106; C12Q 2600/158; C12Q 2600/178
See application file for complete search history.

(56) References Cited

U.S. PATENT DOCUMENTS

| 11,845,975 B2 * | 12/2023 | Yasui | .................... | G01N 33/493 |
| 2023/0265521 A1 * | 8/2023 | Yasui | .................... | C12Q 1/6806 435/6.11 |

OTHER PUBLICATIONS

Kipps, T.J. et al. Leukemia & Lymphoma 56(10):2826-2833. May 2015. (Year: 2015).*

(Continued)

*Primary Examiner* — Diana B Johannsen
(74) *Attorney, Agent, or Firm* — WCF IP

(57) ABSTRACT

The present invention relates to the stratification and treatment of patients suffering of cancer. Due to the fact that anti-PD1 therapy targets lymphocytes and the efficiency of anti-cancer therapy is measured by the impact on the tumor cells, the inventors postulated that studying the molecular mechanisms of resistance of anti-PD1 therapy should take into consideration existing intercellular communication between lymphocytes and tumor cells. As exosomes are the carriers for the intercellular transfer of the miRNA responsible of chemoresistance, they herein investigated whether exposure of T cells to anti-PD1 therapy might promote the expression of exosomal miRNA (exomiR) causing the chemoresistance of cancer cells. Surprisingly, they found (Continued)

Figure 1A:
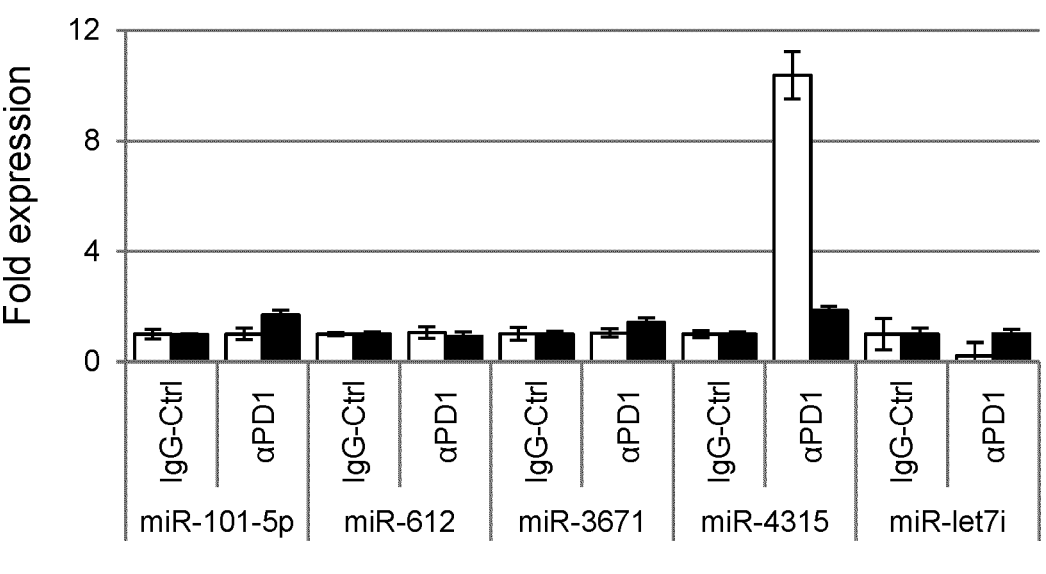

that anti-PD1 exposure of T-cell promotes an enrichment of exosomal miRNA-4315. They also noted that exosomal miRNA-4315 induced a phenomenon of apopto-resistance to conventional chemotherapies in cancer cells receiving exosomal miRNA-4315. At molecular level, they discern that the apopto-resistance phenomenon was associated with the miRNA-4315-mediated down-regulation of Bim, a pro-apoptotic protein. In cellular and mice models, they observed that the BH3 mimetic agent ABT263 circumvented this resistance. Thus, the invention relates to methods of stratification using exosomal miRNA-4315 and method of treatment of patients suffering of cancer using BH3 mimetic agent.

10 Claims, 6 Drawing Sheets

Specification includes a Sequence Listing.

(56)                    References Cited

OTHER PUBLICATIONS

Lever, J.R. et al. Pharmacological Research 142:87-100.Feb. 2019. (Year: 2019).*

Peng Xiao-Xiao et al, "Correlation of plasma exosomal microRNAs with the efficacy of immunotherapy in EGFR/ALK wild-type advanced non-small cell lung cancer", Journal for Immunotherapy of Cancer, vol. 8, No. 1, Jan. 1, 2020 (Jan. 1, 2020), p. e000376.

Genova C. et al, "1277P An exosomal miRNA signature as predictor of benefit from immune checkpoint inhibitors in non-small cell lung cancer", NL vol. 31 Sep. 19, 2020.

Ernest Y. Lee et al, "Circulating biomarkers predictive of tumor response to cancer immunotherapy", Expert Reviews in Molecular Diagnostics, vol. 19, No. 10, Sep. 10, 2019 (Sep. 10, 2019), p. 895-904.

Fan Jinshuo et al, "Circulating microRNAs predict the response to anti-PD-1 therapy in non-small cell lung cancer", Nov. 28, 2019 (Nov. 28, 2019), vol. 112, No. 2, p. 2063-2071.

Janine Scholefield et al, "Design of RNAi Hairpins for Mutation-Specific Silencing of Ataxin-7 and Correction of a SCA7 Phenotype", PLOS ONE, vol. 4, No. 9, Sep. 30, 2009 (Sep. 30, 2009), p. e7232.

Zhang et al, "BH3 mimetics to improve cancer therapy; mechanisms and examples", Drug Resistance Updates, Churchill Livingstone, Edinburgh, GB, vol. 10, No. 6, Oct. 24, 2007 (Oct. 24, 2007), p. 207-217.

Guyon Nina et al, "Anti-PD1 therapy induces lymphocyte-derived exosomal miRNA-4315 release inhibiting Bim-mediated apoptosis of tumor cells", vol. 11, No. 12 online Dec. 11, 2020.

* cited by examiner

α-amanitin (50µg/ml)

SEQUENCE LISTING

<160> NUMBER OF SEQ ID NOS: 3

<210> SEQ ID NO 1
<211> LENGTH: 18
<212> TYPE: RNA
<213> ORGANISM: Homo sapiens

<400> SEQUENCE: 1
ccgcuuucug agcuggac                                                                          18

<210> SEQ ID NO 2
<211> LENGTH: 18
<212> TYPE: RNA
<213> ORGANISM: Artificial Sequence
<220> FEATURE:
<223> OTHER INFORMATION: Synthetic mimic

<400> SEQUENCE: 2
ccgcuuucug agcuggac                                                                          18

<210> SEQ ID NO 3
<211> LENGTH: 18
<212> TYPE: RNA
<213> ORGANISM: Artificial Sequence
<220> FEATURE:
<223> OTHER INFORMATION: Synthetic mimic

<400> SEQUENCE: 3
ccgaaaucug agcuggac                                                                          18

METHOD TO TREAT AND STRATIFY A PATIENT SUFFERING FROM A CANCER

FIELD OF THE INVENTION

The present invention relates to the stratification and treatment of patients suffering of cancer.

BACKGROUND OF THE INVENTION

Immune checkpoint inhibitors, in first line or in combination with conventional chemotherapy, have shown great promise as anti-cancer treatment (1). Anti-PD1 therapy is, to date, one of the most effective anticancer immunotherapies. Despite this success, a significant number of patients develop, or will develop, resistance to this therapy (2-3-4-5). Innate resistance to anti-PD1 therapy is found in 60% of melanoma patients (6), and 25% develop resistance after an initial phase of objective response (7). In non-small-cell lung carcinoma, Gettinger et al. identified patients characterized by a phenomenon of acquired resistance to anti-PD1 therapy (8). Whereas resistance to anti-PD1 therapy is observed in clinical practice, its molecular causes have not been fully documented. Consequently, extensive researches need to be performed in order to complete the description of biomarkers associated with the resistance to anti-PD-1 therapy. In addition, the description of these innovative biomarkers could provide therapeutic targets against the anti-PD1-induced resistance.

SUMMARY OF THE INVENTION

Due to the fact that anti-PD1 therapy targets lymphocytes and the efficiency of anti-cancer therapy is measured by the impact on the tumor cells, the inventors postulated that studying the molecular mechanisms of resistance of anti-PD1 therapy should take into consideration existing intercellular communication between lymphocytes and tumor cells. As exosomes are the carriers for the intercellular transfer of the miRNA responsible of chemoresistance (9-10-11-12), they herein investigated whether exposure of T cells to anti-PD1 therapy might promote the expression of exosomal miRNA (exomiR) causing the chemoresistance of cancer cells. Surprisingly, they found that anti-PD1 exposure of T-cell promotes an enrichment of exosomal miRNA-4315. They also noted that exosomal miRNA-4315 induced a phenomenon of apopto-resistance to conventional chemotherapies in cancer cells receiving exosomal miRNA-4315. At molecular level, they discern that the apopto-resistance phenomenon was associated with the miRNA-4315-mediated down-regulation of Bim, a pro-apoptotic protein. In cellular and mice models, they observed that the BH3 mimetic agent ABT263 circumvented this resistance. Finally, a longitudinal study using patient blood showed that miRNA-4315 and cytochrome c can be used to define the time period during which the addition of ABT263 therapy may effectively increase cancer cell death and bypass anti-PD1 resistance. Thank to this work, the inventors showed that the exosomal miRNA-4315 can be used as a blood biomarker for patient stratification developing a phenomenon of resistance to anti-PD1 antibody therapy and identified a therapeutic alternative (the use of a BH3 mimetic drug) to limit this resistance phenomenon.

Thus, the present invention relates to methods of stratification using exosomal miRNA-4315 and method of treatment of patients suffering of cancer using BH3 mimetic agent. Particularly, the invention is defined by its claims.

DETAILED DESCRIPTION OF THE INVENTION

Prognostic Method

In a first aspect, the invention relates to a method of identifying a patient having or at risk of having or developing a resistance to anti-PD-1 therapy comprising the steps consisting of i) determining the expression level of the exosomal miRNA-4315 in a sample from said patient, ii) comparing said expression level with a predetermined reference value and iii) concluding that the patient has or is at risk of having or developing a resistance to the anti-PD1 therapy when the expression level of the exosomal miRNA-4315 is superior to the predetermined reference value and concluding that the patient has not or is not at risk of having or not develop a resistance to the anti-PD1 therapy when the expression level of the exosomal miRNA-4315 is inferior to the predetermined reference value.

In other words, the invention relates to a method of stratification of a patient treated by anti-PD-1 therapy.

The invention also relates to a method for predicting an anti-PD-1 therapy response of a patient suffering from a cancer in need thereof, comprising i) determining in a sample obtained from the patient the expression level of the exosomal miRNA-4315 ii) comparing said expression level with a predetermined reference value and iii) concluding that the patient will not respond to the anti-PD1 therapy when the expression level of the exosomal miRNA-4315 is superior to the predetermined reference value and concluding that the patient will respond to the anti-PD1 therapy when the expression level of the exosomal miRNA-4315 is inferior to the predetermined reference value.

According to the invention, the methods of the invention are particularly in vitro methods.

In one embodiment, the cancer may be any solid or liquid cancer. Typically, the cancer may be selected from the group consisting of bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, glioblastoma, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating, lobular carcinoma, lobular carcinoma in, situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinroma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

In a particular embodiment, the cancer is a glioblastoma (GBM), a lung cancer, a breast cancer or an ovarian cancer.

In a particular embodiment, the glioblastoma is a glioblastoma multiforme (GBM) and the lung cancer is a lung adenocarcinoma.

Typically, the sample according to the invention may be blood, plasma, serum sample, T cell-derived exosomes or a cancer biopsy.

According to the invention, the term "patient" or "subject" denotes a mammal, such as a rodent, a feline, a canine, and a primate. In some embodiments, the subject is a human. In some embodiments, the subject is a human infant. Particularly, the subject denotes a human with a cancer and particularly a GBM, a lung cancer, a breast cancer or an ovarian cancer.

As used herein, the term "miRNA-4315" denotes a miRNA gene located on chromosome 17 (17q21.31) and is accessible in the miRBase database under the ID number: MI0015844.

Particularly, the miRNA-4315 is the hsa-mir-4315-1 and has the nucleic acid sequence of the mature miRNA-4315 is (5'-3'): CCGCUUUCUGAGCUGGAC (SEQ ID NO: 1)

As used herein the term "exosomal miRNA-4315" denotes the presence of the miRNA-4315 in exosomes. In a particular embodiment, the "exosomal miRNA-4315" are exosomes containing the miRNA-4315 derived from T cells exposed to the anti-PD-1 therapy.

As used herein, the term "the expression level of the exosomal miRNA-4315" or 'the level the exosomal miRNA-4315" of denotes the level of exosomal miRNA-4315 compared to the total of miRNA-4315.

As used herein, the term "anti-PD-1 therapy denotes the use of at least one antibody anti-PD-1 to treat the cancer of the patient. For example, the antibody anti-PD-1 can be the nivolumab, the pembrolizumab or the cemiplimab.

In a particular embodiment, the patient may receive simultaneously, separately or in a sequential manner a standard chemotherapy with the anti-PD-1 therapy.

As used herein, the term "standard chemotherapy" denotes a classical anti-cancer agent selected in the group consisting but not limited to cytarabine, anthracyclines, fludarabine, gemcitabine, capecitabine, methotrexate, taxol, taxotere, mercaptopurine, thioguanine, hydroxyurea, cyclophosphamide, ifosfamide, nitrosoureas, platinum complexes such as cisplatin, carboplatin and oxaliplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin A. In one embodiment, additional anticancer agents may be selected from, but are not limited to, one or a combination of the following class of agents: alkylating agents, plant alkaloids, DNA topoisomerase inhibitors, anti-folates, pyrimidine analogs, purine analogs, DNA antimetabolites, taxanes, podophyllotoxin, hormonal therapies, retinoids, photosensitizers or photodynamic therapies, angiogenesis inhibitors, antimitotic agents, isoprenylation inhibitors, cell cycle inhibitors, actinomycins, bleomycins, MDR inhibitors and Ca2+ ATPase inhibitors.

Particularly, the standard chemotherapy can be the oxaliplatin, the cisplatin, the temozolomide, the cyclophosphamide, the doxorubicin or the paclitaxel.

In another embodiment, the patient affected with a cancer and particularly a glioblastoma can also be treated with a standard treatment consisting of maximal surgical resection, radiotherapy, and concomitant adjuvant standard chemotherapy like temozolomide.

In one embodiment and according to the methods of the invention, the determination of the expression level of the exosomal miRNA-4315 of the invention may be determined before or after the beginning of a treatment with the anti-PD-1 therapy of the patient.

The term "determining the expression level of" as used above includes qualitative and/or quantitative detection (measuring levels) with or without reference to a control. Typically expression level of the miR of the invention may be measured for example by RNA-immunoprecipitation, Cross-linking immunoprecipitation, qRT-PCR performed and all RNA sequencing methods on the sample.

The "reference value" may be a healthy subject, i.e. a subject who does not suffer from any cancer and particularly glioblastoma. Particularly, said control is a not an healthy subject. In another embodiment, the "reference value" may be a subject having a cancer without resistance to anti-PD-1 therapy.

Measuring the expression level of a miR can be performed by a variety of techniques well known in the art. In the case of the invention, before determining the level of the miR of the invention, the exosomes derived from T cells (T cell-derived exosomes) will be isolated and quantified by any technique allowing that (see for example the materials and methods part of the application). Particular, the "Exo-Quick" (see the materials and methods part) can be used to isolate the exosomes.

Methods for determining the quantity of miR are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted miR is then detected by hybridization (e. g., Northern blot analysis, in situ hybridization) and/or amplification (e.g., RT-PCR).

Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the miR of interest herein find utility as hybridization probes or amplification primers. It is understood that such nucleic acids need not be identical, but are typically at least about 80% identical to the homologous region of comparable size, more particularly 85% identical and even more particularly 90-95% identical. In certain embodiments, it will be advantageous to use nucleic acids in combination with appropriate means, such as a detectable label, for detecting hybridization.

Typically, the nucleic acid probes include one or more labels, for example to permit detection of a target nucleic acid molecule using the disclosed probes. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or concentration of a target nucleic acid sequence (e.g., genomic target nucleic acid sequence) (to which the labeled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultraviolet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook—A Guide to Fluorescent Probes and Labeling Technologies). Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl) aminonaphthalene-1-sulfonic acid (EDANS), 4-amino-N-[3 vinylsulfonyl)phenyl]naphthalimide-3,5 disulfonate (Lucifer Yellow VS), N-(4-anilino-1-naphthyl)maleimide, antl1ranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diarninidino-2-phenylindole (DAPI); 5',5"dibromopyrogallol-sulfonephthalein (Bromopyrogallol Red); 7-diethylamino-3 (4'-isothiocyanatophenyl)-4-methylcoumarin; diethylenetriamine pentaacetate; 4,4'-diisothiocyanatodihydrostilbene-2,2'-disulfonic acid; 4,4'-diisothiocyanatostilbene-2,2'-disulforlic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6di-clllorotriazin-2-yDarninofluorescein (DTAF), 2'7'dimethoxy-4'5'-dichloro-6-carboxyfluorescein (JOE), fluorescein, fluorescein isothiocyanate (FITC), and QFITC Q(RITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6, 130, 101 and 6,716,979), the BODIPY series of dyes (dipyrrometheneboron difluoride dyes, for example as described in U.S. Pat. Nos. 4,774,339, 5,187,288, 5,248,782, 5,274,113, 5,338, 854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (Quantum-Dot Corp, Invitrogen Nanocrystal Technologies, Eugene, Oreg.); see also, U.S. Pat. Nos. 6,815,064; 6,682,596; and 6,649, 138). Semiconductor nanocrystals are microscopic particles having size-dependent optical and/or electrical properties. When semiconductor nanocrystals are illuminated with a primary energy source, a secondary emission of energy occurs of a frequency that corresponds to the handgap of the semiconductor material used in the semiconductor nanocrystal. This emission can he detected as colored light of a specific wavelength or fluorescence. Semiconductor nanocrystals with different spectral characteristics are described in e.g., U.S. Pat. No. 6,602,671. Semiconductor nanocrystals that can he coupled to a variety of biological molecules (including dNTPs and/or nucleic acids) or substrates by techniques described in, for example, Bruchez et al., Science 281:20132016, 1998; Chan et al., Science 281: 2016-2018, 1998; and U.S. Pat. No. 6,274,323. Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Puhlication No. 2003/0165951 as well as PCT Puhlication No. 99/26299 (puhlished May 27, 1999). Separate populations of semiconductor nanocrystals can he produced that are identifiable based on their different spectral characteristics. For example, semiconductor nanocrystals can he produced that emit light of different colors based on their composition, size or size and composition. For example, quantum dots that emit light at different wavelengths based on size (565 mn, 655 mn, 705 mn, or 800 mn emission wavelengths), which are suitable as fluorescent labels in the probes disclosed herein are available from Life Technologies (Carlshad, Calif).

Additional labels include, for example, radioisotopes (such as 3 H), metal chelates such as DOTA and DPTA chelates of radioactive or paramagnetic metal ions like Gd3+, and liposomes.

Detectable labels that can be used with nucleic acid molecules also include enzymes, for example horseradish peroxidase, alkaline phosphatase, acid phosphatase, glucose oxidase, beta-galactosidase, beta-glucuronidase, or beta-lactamase.

Alternatively, an enzyme can be used in a metallographic detection scheme. For example, silver in situ hyhridization (SISH) procedures involve metallographic detection schemes for identification and localization of a hybridized genomic target nucleic acid sequence. Metallographic detection methods include using an enzyme, such as alkaline phosphatase, in combination with a water-soluble metal ion and a redox-inactive substrate of the enzyme. The substrate is converted to a redox-active agent by the enzyme, and the redoxactive agent reduces the metal ion, causing it to form a detectable precipitate. (See, for example, U.S. Patent Application Puhlication No. 2005/0100976, PCT Publication No. 2005/15 003777 and U.S. Patent Application Publication No. 2004/0265922). Metallographic detection methods also include using an oxido-reductase enzyme (such as horseradish peroxidase) along with a water soluble metal ion, an oxidizing agent and a reducing agent, again to form a detectable precipitate. (See, for example, U.S. Pat. No. 6,670,113).

Probes made using the disclosed methods can be used for nucleic acid detection, such as ISH procedures (for example, fluorescence in situ hybridization (FISH), chromogenic in situ hybridization (CISH) and silver in situ hybridization (SISH)) or comparative genomic hybridization (CGH).

In situ hybridization (ISH) involves contacting a sample containing target nucleic acid sequence (e.g., genomic target nucleic acid sequence) in the context of a metaphase or interphase chromosome preparation (such as a cell or tissue sample mounted on a slide) with a labeled probe specifically hybridizable or specific for the target nucleic acid sequence (e.g., genomic target nucleic acid sequence). The slides are optionally pretreated, e.g., to remove paraffin or other materials that can interfere with uniform hybridization. The sample and the probe are both treated, for example by heating to denature the double stranded nucleic acids. The probe (formulated in a suitable hybridization buffer) and the sample are combined, under conditions and for sufficient time to permit hybridization to occur (typically to reach equilibrium). The chromosome preparation is washed to remove excess probe, and detection of specific labeling of the chromosome target is performed using standard techniques.

For example, a biotinylated probe can be detected using fluorescein-labeled avidin or avidin-alkaline phosphatase. For fluorochrome detection, the fluorochrome can be detected directly, or the samples can be incubated, for example, with fluorescein isothiocyanate (FITC)-conjugated avidin. Amplification of the FITC signal can be effected, if necessary, by incubation with biotin-conjugated goat antiavidin antibodies, washing and a second incubation with FITC-conjugated avidin. For detection by enzyme activity, samples can be incubated, for example, with streptavidin, washed, incubated with biotin-conjugated alkaline phosphatase, washed again and pre-equilibrated (e.g., in alkaline phosphatase (AP) buffer). For a general description of in situ hybridization procedures, see, e.g., U.S. Pat. No. 4,888,278.

Numerous procedures for FISH, CISH, and SISH are known in the art. For example, procedures for performing FISH are described in U.S. Pat. Nos. 5,447,841; 5,472,842; and 5,427,932; and for example, in Pirlkel et al., Proc. Natl. Acad. Sci. 83:2934-2938, 1986; Pinkel et al., Proc. Natl. Acad. Sci. 85:9138-9142, 1988; and Lichter et al., Proc. Natl. Acad. Sci. 85:9664-9668, 1988. CISH is described in, e.g., Tanner et al., Am. 1. Pathol. 157:1467-1472, 2000 and U.S. Pat. No. 6,942,970. Additional detection methods are provided in U.S. Pat. No. 6,280,929.

Numerous reagents and detection schemes can be employed in conjunction with FISH, CISH, and SISH procedures to improve sensitivity, resolution, or other desirable properties. As discussed above probes labeled with fluorophores (including fluorescent dyes and QUANTUM DOTS®) can be directly optically detected when performing FISH. Alternatively, the probe can be labeled with a non-fluorescent molecule, such as a hapten (such as the following non-limiting examples: biotin, digoxigenin, DNP, and various oxazoles, pyrrazoles, thiazoles, nitroaryls, benzofurazans, triterpenes, ureas, thioureas, rotenones, coumarin, courmarin-based compounds, Podophyllotoxin, Podophyllotoxin-based compounds, and combinations thereof), ligand or other indirectly detectable moiety. Probes labeled with such non-fluorescent molecules (and the target nucleic acid sequences to which they bind) can then be detected by contacting the sample (e.g., the cell or tissue sample to which the probe is bound) with a labeled detection reagent, such as an antibody (or receptor, or other specific binding partner) specific for the chosen hapten or ligand. The detection reagent can be labeled with a fluorophore (e.g., QUANTUM DOT®) or with another indirectly detectable moiety, or can be contacted with one or more additional specific binding agents (e.g., secondary or specific antibodies), which can be labeled with a fluorophore.

In other examples, the probe, or specific binding agent (such as an antibody, e.g., a primary antibody, receptor or other binding agent) is labeled with an enzyme that is capable of converting a fluorogenic or chromogenic composition into a detectable fluorescent, colored or otherwise detectable signal (e.g., as in deposition of detectable metal particles in SISH). As indicated above, the enzyme can be attached directly or indirectly via a linker to the relevant probe or detection reagent. Examples of suitable reagents (e.g., binding reagents) and chemistries (e.g., linker and attachment chemistries) are described in U.S. Patent Application Publication Nos. 2006/0246524; 2006/0246523, and 2007/01 17153.

It will be appreciated by those of skill in the art that by appropriately selecting labelled probe-specific binding agent pairs, multiplex detection schemes can he produced to facilitate detection of multiple target nucleic acid sequences (e.g., genomic target nucleic acid sequences) in a single assay (e.g., on a single cell or tissue sample or on more than one cell or tissue sample). For example, a first probe that corresponds to a first target sequence can he labelled with a first hapten, such as biotin, while a second probe that corresponds to a second target sequence can be labelled with a second hapten, such as DNP. Following exposure of the sample to the probes, the bound probes can he detected by contacting the sample with a first specific binding agent (in this case avidin labelled with a first fluorophore, for example, a first spectrally distinct QUANTUM DOT®, e.g., that emits at 585 mn) and a second specific binding agent (in this case an anti-DNP antibody, or antibody fragment, labelled with a second fluorophore (for example, a second spectrally distinct QUANTUM DOT®, e.g., that emits at 705 mn). Additional probes/binding agent pairs can he added to the multiplex detection scheme using other spectrally distinct fluorophores. Numerous variations of direct, and indirect (one step, two step or more) can he envisioned, all of which are suitable in the context of the disclosed probes and assays.

Probes typically comprise single-stranded nucleic acids of between 10 to 1000 nucleotides in length, for instance of between 10 and 800, more particularly of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they particularly hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A particular kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise the steps of providing total miR extracted from cumulus cells and subjecting the miR to amplification and hybridization to specific probes, more particularly by means of a quantitative or semi-quantitative RT-PCR.

In another particular embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

Expression level of a gene may be expressed as absolute expression level or normalized expression level. Typically, expression levels are normalized by correcting the absolute expression level of a gene by comparing its expression to the expression of a gene that is not a relevant for determining the cancer stage of the patient, e.g., a housekeeping gene that is constitutively expressed. Suitable genes for normalization include housekeeping genes such as the actin gene ACTB, ribosomal 18S gene, GUSB, PGK1 and TFRC. According to the invention the housekeeping genes used were GAPDH, GUSB, TBP and ABL1. This normalization allows the comparison of the expression level in one sample, e.g., a patient sample, to another sample, or between samples from different sources.

Typically, a "threshold value", "threshold level", "reference value" or "cut-off value" can be determined experimentally, empirically, or theoretically. A threshold value can also be arbitrarily selected based upon the existing experimental and/or clinical conditions, as would be recognized by a person of ordinary skilled in the art. Particularly, the person skilled in the art may compare the expression levels of the miR of the invention obtained according to the method of the invention with a defined threshold value.

Particularly, said threshold value is the mean expression level of the miR of the invention of a population of healthy individuals. As used herein, the term "healthy individual" denotes a human which is known to be healthy, i.e. which does not suffer from a cancer and in particular from a glioblastoma and does not need any medical care.

Typically, the skilled person in the art may determine the expression level of the miR of the invention in a biological sample, particularly a biopsy of a glioblastoma cancer for example, of 100 individuals known to be healthy or not. The mean value of the obtained expression levels is then determined, according to well-known statistical analysis, so as to obtain the mean expression level of the miR of the invention. Said value is then considered as being normal and thus constitutes a threshold value. By comparing the expression levels of the miR of the invention to this threshold value, the physician is then able to classify and prognostic the cancer.

Accordingly, the physician would be able to adapt and optimize appropriate medical care of a patient in a critical and life-threatening condition suffering from cancer. The determination of said prognosis is highly appropriate for follow-up care and clinical decision making.

The present invention also relates to kits useful for the methods of the invention, comprising means for detecting the miR of the invention.

Therapeutic Method

A second aspect of the invention relates to a BH3 mimetic agent for use in the treatment of a cancer in a subject identified as having or which will have or develop a resistance to anti-PD-1 therapy according to the invention.

In other word, the invention relates to a BH3 mimetic agent for use in the treatment of a subject which will not respond to an anti-PD-1 therapy according to the invention.

Thus, the invention also relates to a method of identifying a patient having or at risk of having or developing a resistance to anti-PD-1 therapy comprising the steps consisting of i) determining the expression level of the exosomal miRNA-4315 in a sample from said patient, ii) comparing said expression level with a predetermined reference value and iii) concluding that the patient has or is at risk of having or develop a resistance to the anti-PD1 therapy when the expression level of the exosomal miRNA-4315 is superior to the predetermined reference value and concluding that the patient has not or is not at risk of having or not develop a resistance to the anti-PD1 therapy when the expression level of the exosomal miRNA-4315 is inferior to the predetermined reference value and wherein a BH3 mimetic agent will be administrated to the patient which has or which is at risk of having or developing a resistance to the anti-PD1 therapy.

In other word, the invention relates to a method for predicting an anti-PD-1 therapy response of a patient suffering from a cancer in need thereof, comprising i) determining in a sample obtained from the patient the expression level of the exosomal miRNA-4315 ii) comparing said expression level with a predetermined reference value and iii) concluding that the patient will not respond to the anti-PD1 therapy when the expression level of the exosomal miRNA-4315 is superior to the predetermined reference value and concluding that the patient will respond to the anti-PD1 therapy when the expression level of the exosomal miRNA-4315 is inferior to the predetermined reference value and wherein a BH3 mimetic agent will be administrated to the patient which will not respond to the anti-PD1 therapy.

As used herein, the term "BH3 mimetic agent" denotes all compounds which have an action (inhibition) on Bcl-2, an anti-apoptotic protein and include all small molecules capable of mimicking BH3-only proteins and thus inducing apoptosis (see for example Haiming Dai et al. Mitochondrial apoptosis and BH3 mimetics. 2016). BH3 mimetic agent can be selected in the group consisting in: ABT-737, venetoclax (ABT-199) and navitoclax (ABT-263).

In another embodiment, the invention also relates to an anti-miRNA-4315 (antago-miR) for use in the treatment of a cancer in a subject identified as having or which will have or develop a resistance to anti-PD-1 therapy according to the invention.

In other word, the invention relates to an anti-miRNA-4315 (antago-miR) for use in the treatment of a subject which will not respond to an anti-PD-1 therapy according to the invention.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

The invention also relates to i) an anti-PD-1 therapy and ii) a BH3 mimetic agent, as a combined preparation for simultaneous, separate or sequential for use in the treatment of a cancer in a subject identified as having or which will have or develop a resistance to anti-PD-1 therapy according to the invention.

The invention also relates to i) an anti-PD-1 therapy and ii) a BH3 mimetic agent, as a combined preparation for simultaneous, separate or sequential for use in the treatment of a cancer in a subject which will not respond to the anti-PD1 therapy according to the invention.

The invention also relates to i) an anti-PD-1 therapy, ii) a BH3 mimetic agent and iii) standard chemotherapy according to the invention, as a combined preparation for simultaneous, separate or sequential for use in the treatment of a cancer in a subject identified as having or which will have or develop a resistance to anti-PD-1 therapy according to the invention.

The invention also relates to i) an anti-PD-1 therapy, ii) a BH3 mimetic agent and iii) standard chemotherapy according to the invention, as a combined preparation for simultaneous, separate or sequential for use in the treatment of a cancer in a subject which will not respond to the anti-PD1 therapy according to the invention.

In a particular embodiment, the subject can also be treated by radiotherapy or by a radiotherapeutic agent.

As used herein, "radiotherapy" may consist of gamma-radiation, X-ray radiation, electrons or photons, external radiotherapy or curitherapy.

As used herein, the term "radiotherapeutic agent", is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

In one embodiment, the cancer according to the invention is a GBM, a lung cancer, a breast cancer or an ovarian cancer.

In one embodiment and according to the method of treatment, the cancer may be any solid or liquid cancer. Typically, the cancer may be selected from the group consisting of bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, glioblastoma, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating, lobular carcinoma, lobular carcinoma in, situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinroma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

In a particular embodiment, the glioblastoma is a GBM, a lung cancer, a breast cancer or an ovarian cancer.

Another object of the invention relates to a method for treating cancer comprising administrating to a subject identified as having or which will have or develop a resistance to anti-PD-1 therapy according to the invention a therapeutically effective amount of a BH3 mimetic agent.

Therapeutic Composition

Another object of the invention relates to a therapeutic composition comprising a BH3 mimetic agent according to the invention for use in the treatment of cancer in a subject identified as having or which will have or develop a resistance to anti-PD-1 therapy according to the invention.

In still another object of the invention relates to a therapeutic composition comprising a BH3 mimetic agent according to the invention for use in the treatment of cancer in a subject will not respond to an anti-PD-1 therapy according to the invention.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular or subcutaneous administration and the like.

Particularly, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used.

Pharmaceutical compositions of the present invention may comprise a further therapeutic active agent. The present invention also relates to a kit comprising a compound according to the invention and a further therapeutic active agent.

In one embodiment said therapeutic active agent may be an anti-cancer agent.

Anti-cancer agents may be Melphalan, Vincristine (Oncovin), Cyclophosphamide (Cytoxan), Etoposide (VP-16), Doxorubicin (Adriamycin), Liposomal doxorubicin (Doxil) and Bendamustine (Treanda).

Others anti-cancer agents may be for example cytarabine, anthracyclines, fludarabine, gemcitabine, capecitabine, methotrexate, taxol, taxotere, mercaptopurine, thioguanine, hydroxyurea, cyclophosphamide, ifosfamide, nitrosoureas, platinum complexes such as cisplatin, carboplatin and oxaliplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin A. In one embodiment, additional anticancer agents may be selected from, but are not limited to, one or a combination of the following class of agents: alkylating agents, plant alkaloids, DNA topoisomerase inhibitors, anti-folates, pyrimidine analogs, purine analogs, DNA antimetabolites, taxanes, podophyllotoxin, hormonal therapies, retinoids, photosensitizers or photodynamic therapies, angiogenesis inhibitors, antimitotic agents, isoprenylation inhibitors, cell cycle inhibitors, actinomycins, bleomycins, MDR inhibitors and Ca2+ ATPase inhibitors.

Additional anti-cancer agents may be selected from, but are not limited to, cytokines, chemokines, growth factors, growth inhibitory factors, hormones, soluble receptors, decoy receptors, monoclonal or polyclonal antibodies, mono-specific, bi-specific or multi-specific antibodies, monobodies, polybodies.

Additional anti-cancer agent may be selected from, but are not limited to, growth or hematopoietic factors such as erythropoietin and thrombopoietin, and growth factor mimetics thereof.

In the present methods for treating cancer the further therapeutic active agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoemanolamine, alizapride, azasetron, benzquinamide, bietanautine, bromopride, buclizine, clebopride, cyclizine, dunenhydrinate, diphenidol, dolasetron, meclizme, methallatal, metopimazine, nabilone, oxypemdyl, pipamazine, scopolamine, sulpiride, tetrahydrocannabinols, thiefhylperazine, thioproperazine and tropisetron. In a preferred embodiment, the antiemetic agent is granisetron or ondansetron.

In another embodiment, the further therapeutic active agent can be an hematopoietic colony stimulating factor. Suitable hematopoietic colony stimulating factors include, but are not limited to, filgrastim, sargramostim, molgramostim and epoietin alpha.

In still another embodiment, the other therapeutic active agent can be an opioid or non-opioid analgesic agent. Suitable opioid analgesic agents include, but are not limited to, morphine, heroin, hydromorphone, hydrocodone, oxymorphone, oxycodone, metopon, apomorphine, nomioiphine, etoipbine, buprenorphine, mepeddine, lopermide, anileddine, ethoheptazine, piminidine, betaprodine, diphenoxylate, fentanil, sufentanil, alfentanil, remifentanil, levorphanol, dextromethorphan, phenazodne, pemazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, chlorazepate, clonazepam, chlordiazepoxide and alprazolam.

In yet another embodiment, the further therapeutic active agent can be a checkpoint blockade cancer immunotherapy agent.

Typically, the checkpoint blockade cancer immunotherapy agent is an agent which blocks an immunosuppressive receptor expressed by activated T lymphocytes, such as cytotoxic T lymphocyte-associated protein 4 (CTLA4) and programmed cell death 1 (PDCD1, best known as PD-1), or by NK cells, like various members of the killer cell immunoglobulin-like receptor (KIR) family, or an agent which blocks the principal ligands of these receptors, such as PD-1 ligand CD274 (best known as PD-L1 or B7-H1).

Typically, the checkpoint blockade cancer immunotherapy agent is an antibody.

In some embodiments, the checkpoint blockade cancer immunotherapy agent is an antibody selected from the group consisting of anti-CTLA4 antibodies, anti-PD1 antibodies, anti-PDL1 antibodies, anti-PDL2 antibodies, anti-TIM-3 antibodies, anti-LAG3 antibodies, anti-IDO1 antibodies, anti-TIGIT antibodies, anti-B7H3 antibodies, anti-B7H4 antibodies, anti-BTLA antibodies, and anti-B7H6 antibodies.

The invention will be further illustrated by the following figures and examples. However, these examples and figures should not be interpreted in any way as limiting the scope of the present invention.

FIGURES

FIG. 1: Exosomes of T cells exposed to anti-PD1 therapy decrease the temozolomide-induced cell death via miR-4315. A. On day #14, RT-qPCRs were performed to show that anti-PD-1 exposure increases the exosomal level of miR-4315. B. RT-qPCRs were performed to validate the miR-4315 levels in A172 cells after their exposure to indicated exosomes.

Figure 2:
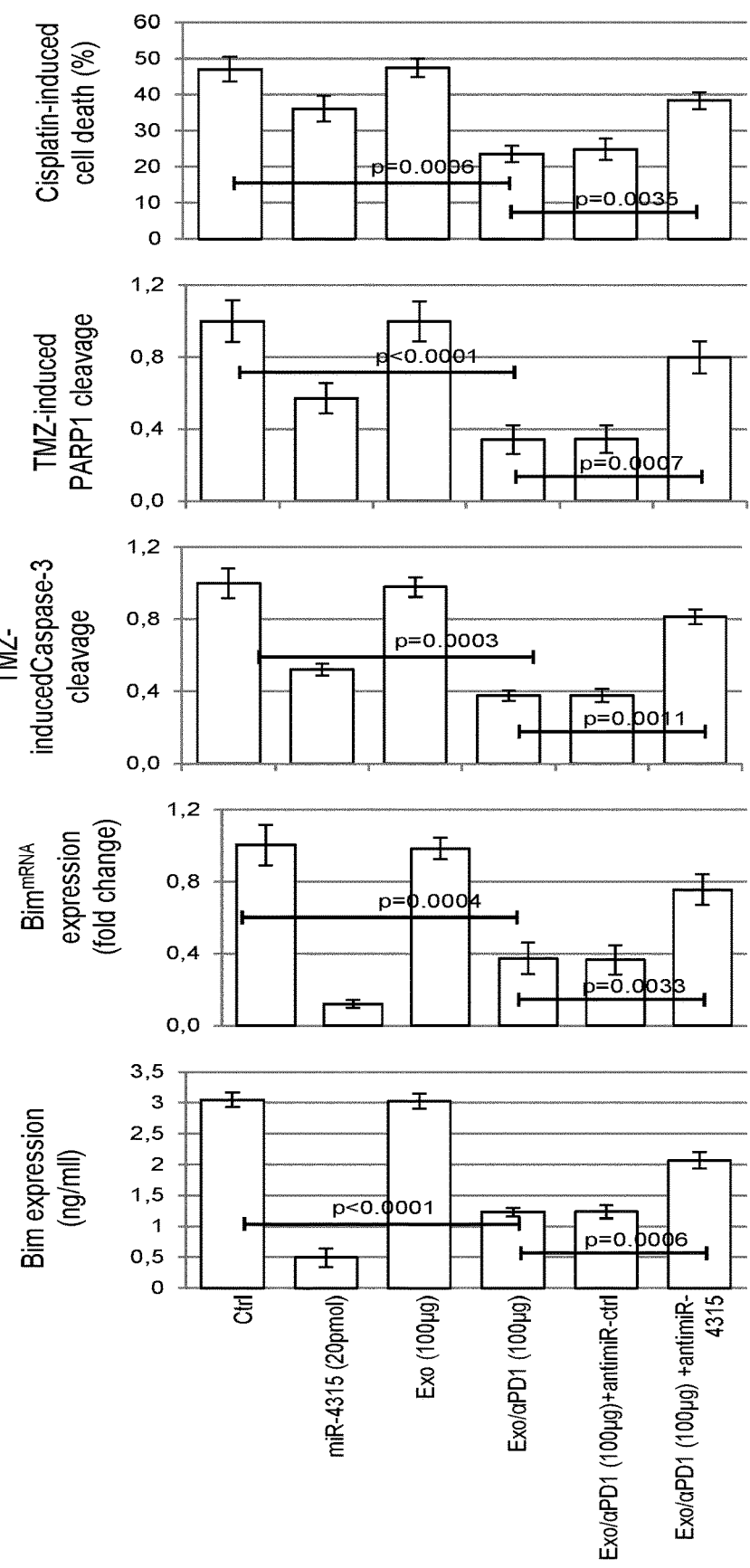

FIG. 2: Exosomes derived from T cells exposed to αPD1 (Exo/αPD1) promote a phenotype of cisplatin-induced apoptosis in A549 cells via miR-4315. Cisplatin-induced cell death measure, PARP and Caspase-3 cleavages were applied to show that exosomes derived from T cells exposed to αPD1 (Exo/αPD1) promote a phenotype of cisplatin-induced apoptosis. RT-qPCR and in-cell ELISA were applied to show that this phenomenon is associated with the miR-4315-mediated down-regulation of Bim.

FIG. 3: Impact of exosomal pretreatment on the cell death induction> by oxaliplatin or paclitaxel on ovarian (OV90) (3A) and breast (MCF7)>cancer cells (3B).

FIG. 4: ABT263 abrogates anti-PD1/exomiR-4315-induced resistance to chemotherapy in an in vivo model of lung cancer. A. Cisplatin-induced cell death measure and PARP and Caspase-3 cleavage studies were applied to show that the phenotype of cisplatin resistance induced by exosomes derived from T cells exposed to αPD1 (Exo/αPD1) was abrogated by the use of ABT263.A Cell. B. Graph represents the impact of treatment on tumor volume. Each treatment included four mice.

EXAMPLE

Material & Methods

Cell Culture

T cells were obtained from Stem Cell Technology (France) and were cultured in RPMI medium supplemented with 10% of fetal bovine serum, 1% penicillin-streptomycin. A172 and MCF7 cells were cultured in DMEM (4.5 g/L glucose) medium supplemented with 10% of fetal bovine serum, 1% penicillin-streptomycin. SKOV3 and A549 cells were cultured in RMPI medium supplemented with 10% of fetal bovine serum, 1% penicillin-streptomycin. MCF7 cells were cultured in EMEM supplemented with 10% of fetal bovine serum, 1% penicillin-streptomycin. All cells were cultivated in a 5% $CO_2$ incubator at a temperature of 37° C.

FOXO1 Activity.

TransAM® FKHR/FOXO1 kit (Active Motif, France) was used to estimate the FOXO1 activity. Briefly, at indicated time and condition, cells were harvested and used for a protein nuclear extraction using the Nuclear Extraction Kit (Active Motif, France). For each point (technical duplicate and independent biologic triplicate), 15 μg of nuclear extract were used following the Active Motif's instructions. ELISA plate O.D. was read on a Victor™x3 spectrophotometer (Perkin-Elmer, France).

Cell Cytotoxicity Assay.

Colorimetric Cell Cytotoxicity Assay Kit (Abcam, France) was used to estimate the cell viability. Briefly, cells were seeded in 96-well plate. After the realization of manufacturer's instruction, absorbance was read at 570 and 605 nm using Victor™x3 spectrophotometer (Perkin-Elmer, France).

Measurement of caspase-3 and poly ADP ribose polymerase (PARP) cleavage.

Levels of cleaved caspase-3 and cleaved PARP are considered as both biomarkers of apoptosis. The measurement of these two parameters was performed using the Human Cleaved PARP1 and Human Cleaved Caspase-3 ELISA Kits (Abcam, France) according to the manufacturer's protocol.

In-Cell ELISA.

In cell ELISA were performed using the Bim Colorimetric Cell-Based ELISA kit (Aviva Systems Biology, France) according to the manufacturer's instructions. Briefly, 5 000 cells were seeded in 96-well plate to be exposed or not to indicated exosome or miRNA. After that, cells were treated with a fixing solution (4% of paraformaldehyde solution) for 10 min at room temperature. Primary antibody was incubated overnight at 4° C. Adequate HRP-conjugated secondary antibodies were incubated for 1 hour at room temperature. Detection was performed at 450 nm.

After washes, cells in each well were incubated with crystal violet solution for 5 min at room temperature, according to the manufacturer's instructions. Absorbance was read at 595 nm, and used to normalize the "Bim signal".

Luciferase Promoter and 3'UTR Reporter Assay.

Cells were seeded in 24-well plates and were transfected with the indicated firefly luciferase constructs together with an SV40-renilla control vector. Lysates were prepared at hr, and luciferase activity was measured using the Dual Luciferase Reporter Assay system (Promega, France) and a luminometer (MicroLumat Plus, EG&G Berthold, France).

Cell-Derived Exosome Isolation.

After anti-PD1 exposure, T cell-derived exosomes were isolated using the ExoQuick kit (Ozyme, France) according to the manufacturer's instructions. In brief, cell culture supernatants were harvested and centrifuged at 3000 g/15 min. The ExoQuick solution was incubated with supernatant at 4° C./overnight. After a first centrifugation (1500 g/30 min), the supernatant was aspirated and the residual solution was centrifuged (1500 g/5 min). The exosome pellet was resuspended in PBS. We measured purified exosome total protein concentrations using the Bradford assay (Bio-Rad Laboratories, France), and purified exosomes were stored at −80° C. until use.

Nanosight experiments indicated that Exoquick preparation is mainly composed of extracellular vescules included in a size range of 80 to 120 nm i.e. a size range defining exosome (Additional file 1). Consequently, the term "exosome" was used in this article.

Cell Treatment with Exosomes and/or miR.

At T0, 7.105 cells were seeded in a 12-well plate. After 1 day, cells were co-incubated with T cell-derived exosomes (150 μg) and a-amanitin (50 ug/ml) (Sigma, France). The residual exosomes were eliminated via 3 cell washes in PBS solution. α-amanitin was used to block the putative miRNA transcription caused by experimental conditions since α-amanitin blocks the DNA-dependent RNA polymerase II activity39. The exosome-delivered quantity of miRNA in the cells was estimated using qRT-PCR by means of the difference in Ct value between α-amanitin-treated cells with or without exosomes.

Exosome Loading with Anti-miRNA.

The exosomes were transfected with anti-miRNA using Exo-Fact Exosome Transfection reagent (Ozyme, France). Briefly, anti-miRNA was incubated with the exosomes (300 μg of exosomal protein) in a shaker for 15 min at 37° C. After the addition of ExoQuick-TC solution to stop the reaction, the mixture was incubated on ice for 30 min. After centrifugation, the transfected exosome pellet was resuspended in 300 μL of PBS before use. We measured purified exosome total protein concentrations using the Bradford assay (Bio-Rad Laboratories, France).

HiPerFect Transfection Reagents (Qiagen, France) were used for the transfection of cells with mimic-miR, mimic-mutated-miR and miR inhibitor (also named anti-miR). These reagents are mimic-miR-4315: 5'CCGC-UUUCUGAGCUGGAC (Syn-hsa-miR-4315 miScript miRNA Mimic), mimic-mutated-miR-4315: 5'CCGAAAUCUGAGCUGGAC, and anti-miR-4315 (miScript miRNA Inhibitor and miScript Inhibitor Neg. Control (Qiagen, France).

Plasma Samples

Plasma was collected from GBM patients treated at the "Institut de Cancérologie de l'Ouest" (ICO, http://www.ico-cancer.fr). All patients recruited gave signed, informed consent. All the samples collected and the associated clinical information were registered in the database (N° DC-2018-3321) validated by the French research ministry. Biological resources were stored at the "Centre de Ressources Biologiques-Tumorothèque" (Institut de Cancérologie de l'Ouest, Saint-Herblain, F44800, France).

Isolating Exosomal miRNA from Blood.

From the blood sample collected in K+EDTA tubes, 4-5 ml of plasma was isolated via two centrifugations (10 min/1900 g/4° C. and 10 min/16000 g/4° C.) of 10 ml whole blood. 1 ml of plasma was processed for the isolation of miRNA using the ExomiRNeasy serum/plasma kit (Qiagen, France) according to the manufacturers instructions.

miRNA RT-qPCR.

miScript II RT with miScriptHiSpec buffer, miScript SYBR Green PCR kits and miScript Primer Assays (Qiagen, France) were used to perform the RT-qPCR on the Rotor-Gene Q (Qiagen, France). Quantification and the purity of the miRNA were analyzed using Qubit (Thermo, France) and Agilent 2100 (Small RNA kit, Agilent, France) respectively, according to the manufacturer's instructions, respectively.

RT-qPCR Analysis.

RNA extract is performed using RNeasy Mini QIAcube Kit and QIAcube (Qiagen, France). RT-qPCRs are performed using QuantiTect Reverse Transcription Kit, Rotor-Gene SYBR Green PCR Kit, QuantiTect Primer Assays and Rotor-Gene Q as real-time thermocycler (Qiagen, France). Reference gene RPLPO was used, with the $2\text{-}\Delta\Delta Ct$ relative quantification method.

In Vivo Experiments.

The experimental procedures using animals were in accordance with Institutional Animal Care guidelines and the French National Committee of Ethics. In addition, all experiments were conducted according to the Regulations for Animal Experimentation at the "Plate-forme Animalerie" in the "Institut de Recherche en Santé de l'Université de Nantes (IRS-15N)" and approved by the French National Committee of Ethics. Cultured A549 cells were harvested by trypsinization, washed and resuspended in saline buffer. Cell suspensions were injected subcutaneously (s.c.) into the flanks of 7-/8-week-old mice (Janvier, France). Tumor volume based on caliper measurements was calculated using the modified ellipsoidal formula (Tumor volume=½(length× width2)).

Statistical Analysis and Results.

Except when indicated, data are representative of the mean and standard deviation calculated from 3 independent experiments. Significance of the differences in means±standard deviations was calculated using the Student-t test. The significance of correlation between two parameters was calculated using Pearson's test. $P < 0.05$ was used as a criterion for statistical significance.

Results

The Exosomes of T Cells Exposed to Anti-PD1 Therapy Decreased Temozolomide-Induced Cell Death Via miR-4315

The effect of anti-PD1 antibody (αPD1) therapy on T cells was analyzed by exposing purified human T cells to αPD1 (data not shown). It has been previously demonstrated that anti-PD1 therapy promoted the transcriptional activity of FoxO1 in T lymphocytes1. In our model, the transcriptional activity of FoxO1 in T cells treated with 1 μg/mL of αPD1 strongly increased (p<0.0001) (data not shown). We thus analyzed the expression of five FoxO1-regulated miRNA (miR-101-5p, miR-612, miR-3671, miR-4315, miR-let7i) according to the predictive study performed with the miR-Gen.v3 program. RT-qPCR confirmed the expression of these five miRNA in T cells (FIG. 1A) and αPD1 treatment did not appear to modify their expression. However, strikingly, miR-4315 was 10 times more expressed in exosomes derived from T cells exposed to αPD1 (Exo/αPD1) than in exosomes derived from T cells exposed to the IgG control (Exo) (FIG. 1A).

Figure 1B:
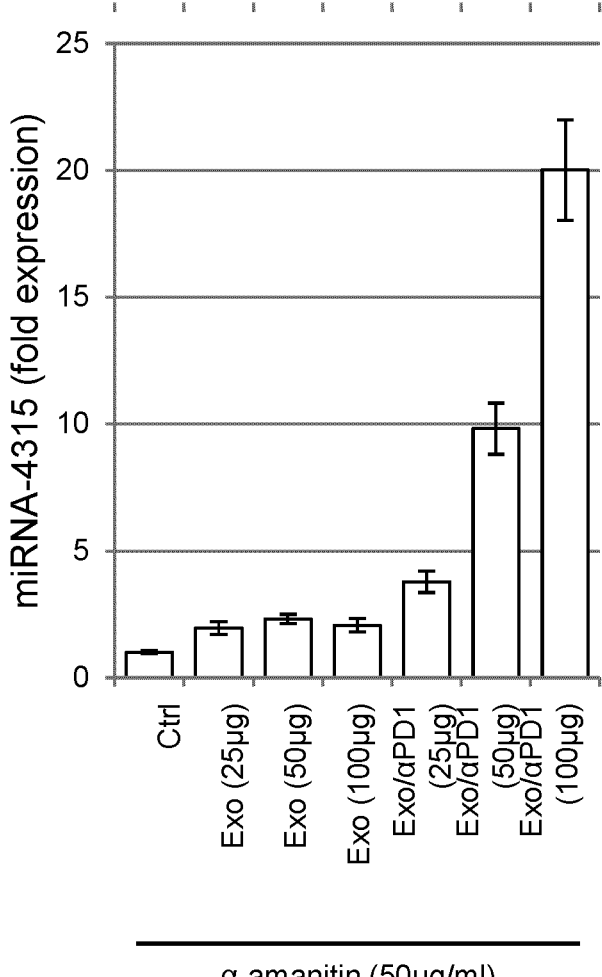

We then analyzed the effect of the exosomes produced by the control or αPD1-treated T cells on the glioma cell line U172. RT-qPCR indicated that the intracellular level of miR-4315 in A172 glioblastoma cells increased in a dose-dependent manner in the presence of Exo/αPD1, α-amanitin and the exosomes derived from T cells exposed to the IgG control (Exo) (FIG. 1B). This observation suggested a possible uptake and transfer of miR-4315 from the Exo/αPD1 to the tumor cells (as α-amanitin was used to block the de novo production of miR-4315).

Temozolomide (TMZ) is the standard chemotherapeutic agent used to kill the glioblastoma (GBM) cells. We therefore studied the TMZ effect on A172 in the presence or absence of Exo/αPD1 by measuring its cytotoxic effect and its ability to induce apoptosis through the detection of the cleaved forms of PARP1 and Caspase-3 (that are two apoptosis biomarkers). In this experiments, cells were exposed for 48h to indicated exosome previous to be treated with TMZ (50 μM, 72h). Thus, we noted that Exo/αPD1 limited the TMZ-induced apoptosis (data not shown). To determine the contribution of miR-4315 in this process, Exo/αPD1 was transfected with an anti-miR-4315. The datas show that the presence of anti-miR-4315 significantly reduced the TMZ-resistance associated with the addition of Exo/αPD1. Overall, our data demonstrated that exosomal miR-4315 limits the apoptosis induced by a chemotherapeutic drug. In addition, this effect is similar to that one seen with miR-4315 alone (data not shown).

Exposure to Anti-PD1 Promotes a Phenotype of Chemotherapy Resistance in Several Cancer Cell Types Via the exomiR-4315/Bim Axis Giving our previous data indicating that exosomal miR-4315 limits apoptosis, we postulated that this miR could target a pro-apoptotic protein in the BCL2 family as these proteins are central to the execution of the apoptosis. The Target Scan Human website suggests that Bim, a pro-apoptotic protein, could be a miR-4315 target (data not shown). We thus focused our study on this protein. A mimic miR-4315, though not an inactive mutant, down-regulated Bim at protein and mRNA levels (data not shown) and decreased the luciferase activity associated with the 3'UTR/Bim plasmid in A172 (data not shown). Exo/αPD1 decreased Bim expression in A172 cells and anti-miR-4315 significantly limited the decrease in Bim expression induced by Exo/αPD1. GW182-CLIP-qPCR indicated that miR-4315 were co-immunoprecipitated with 3'UTR/Bim in A172 cells treated with T-cell-derived Exo/αPD1, but not with T-cell-derived Exo (data not shown). Likewise, anti-miR-4315 also decreased the level of 3'UTR/Bim and miR-4315 co-immunoprecipitated with GW182, while an anti-miR-Ctrl had no effect (data not shown).

Figure 3A:
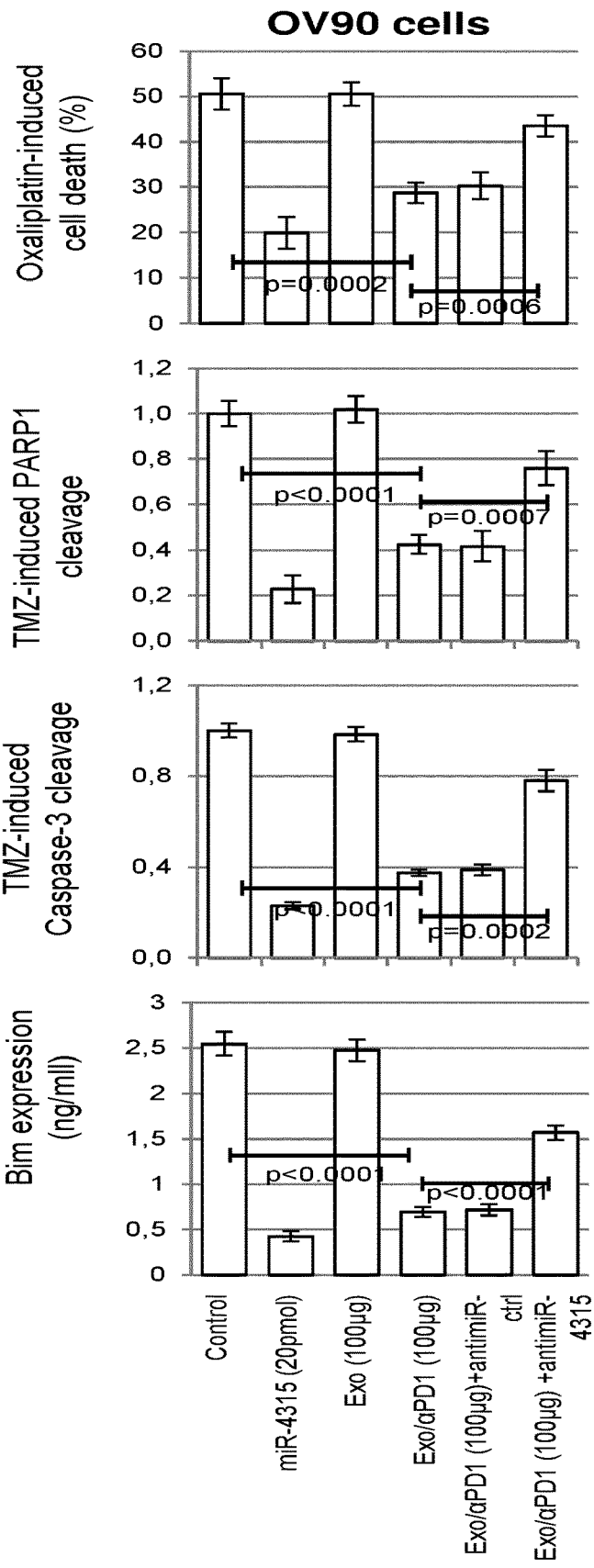
Figure 3B:
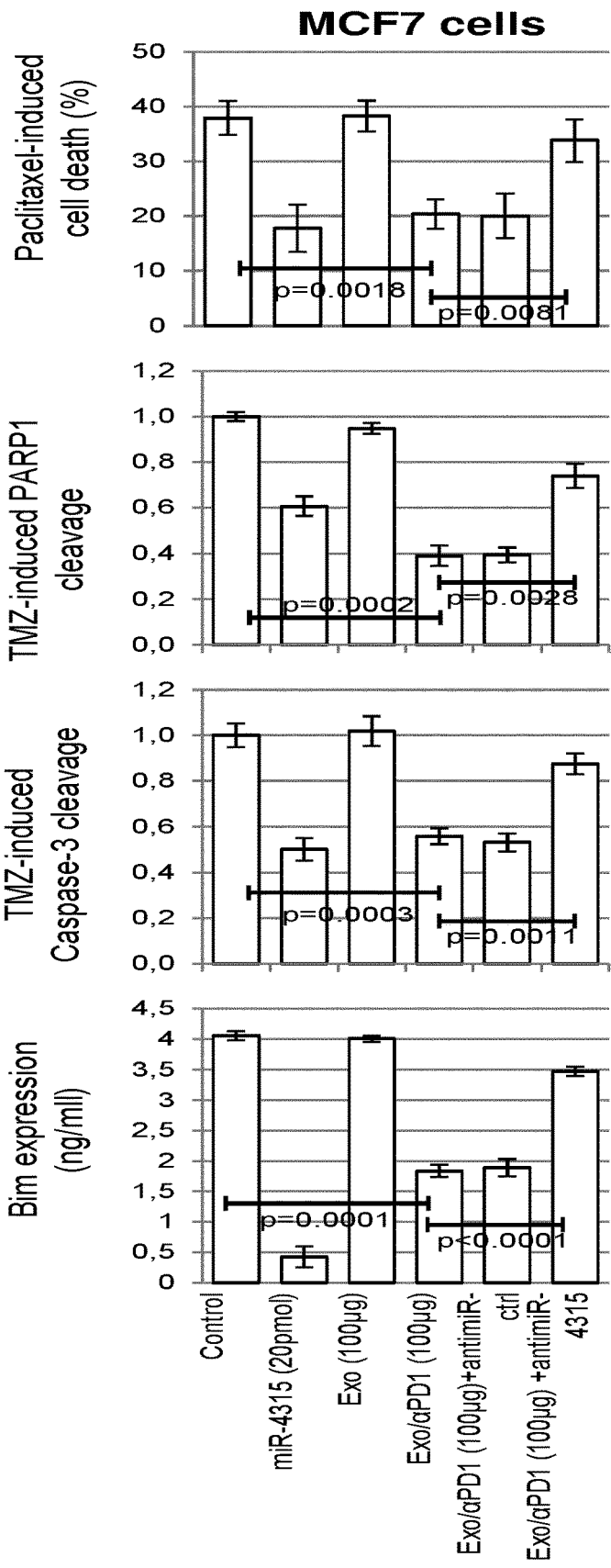

Similar investigations have been carried out on A549 (a lung cancer cell line), OV90 (an ovarian cancer cell line), and MCF7 (a breast carcinoma cancer cell line) treated or not with oxaliplatin, cisplatin and paclitaxel, the respective chemotherapy for each of these cancers. As found with the A172 glioma cell line, Exo/αPD1 decreased the cell death induced by each drug and these effects were counteracted by an anti-miR-4315 (FIG. 2 and FIGS. 3A and 3B). As expected, cell death inhibition was associated with down-regulation of the Bim expression and the decrease of PARP and Caspase-3 cleavage (FIG. 2 and FIGS. 3A and 3B).

Here, we demonstrated that exosomes derived from T cells exposed to αPD1 decreased Bim expression through exomiR-4315. The incorporation of miR-4315 into cancer cell lines in turn led to increased resistance to chemotherapy through the down regulation of apoptosis.

The Longitudinal Expression of exomiR-4315 is Associated with a Serum Biomarker of Apopto-Resistance in Lung Cancer Patients Treated with Anti-PD1 Therapy To determine the clinical relevance of our observations, we examined the exomiR-4315 expression and serum cytochrome c concentrations in 4 patients with lung cancer treated with αPD1 (data not shown). Serum cytochrome c concentration was chosen as a cell death biomarker13. The serum levels of exomiR-4315 and cytochrome c were dynamically regulated throughout the anti-PD1 treatment (data not shown). By comparing the exomiR-4315 expression between two administrations of αPD1 in patients, we noted that the exomiR-4315 expression increased in 10/15 cases. We also observed that exomiR-4315 and serum cytochrome c levels had anti-parallel or mirrored evolution throughout the administration of αPD1 in patients (data not shown). Furthermore, Pearson's correlation test revealed that longitudinal exomiR-4315 expression was inversely correlated with serum cytochrome c concentrations in all patients recruited (data not shown). Overall, these data demonstrate that the longitudinal expression of exomiR-4315 was inversely correlated with a serum biomarker for apoptosis resistance in lung cancer patients treated with αPD1.

Figure 4A:
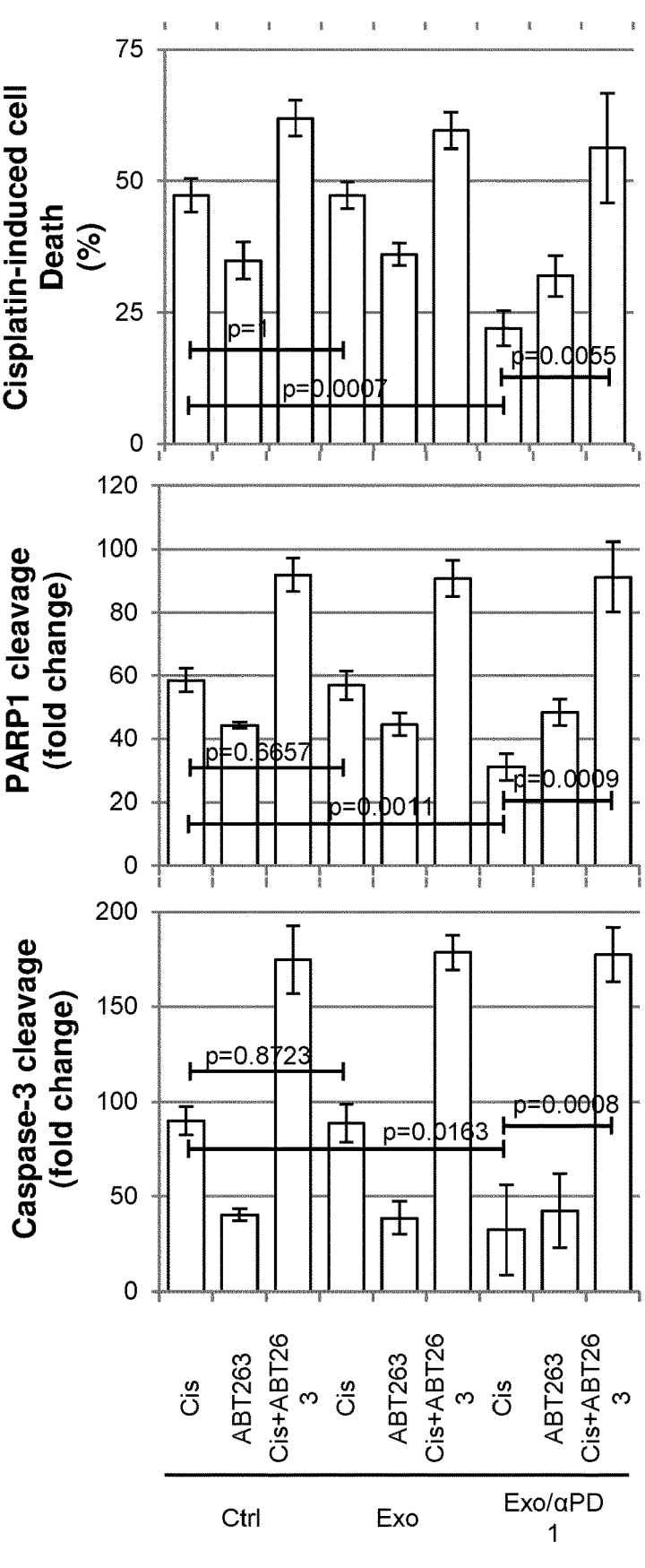

ABT263 Abrogates the Anti-PD1/exomiR-4315-Induced Resistance to Chemotherapy in an In Vivo Model of Lung Cancer The dynamic and anti-parallel expression of the serum levels of exomiR-4315 and cytochrome c suggests that the effectiveness of a treatment in inducing cancer cell death can fluctuate through different phases of effectiveness and ineffectiveness to promote cell death throughout the therapy. In view of the data described above, associating the ineffectiveness of cisplatin+αPD1 therapy with exomiR-4315-induced Bim down-expression, we then studied the effect of a "Bim/BH3 mimetic drug" such as ABT263 on the resistance to cisplatin of A549 cells exposed to Exo/αPD1. A549 lung cancer cells were then exposed to Exo/αPD1 and Exo prior to the addition of cisplatin (CIS, 5 μM) and/or ABT263 (15 μM). ABT263 abrogated the Exo/αPD1-induced resistance to CIS (FIG. 4A).

Figure 4B:
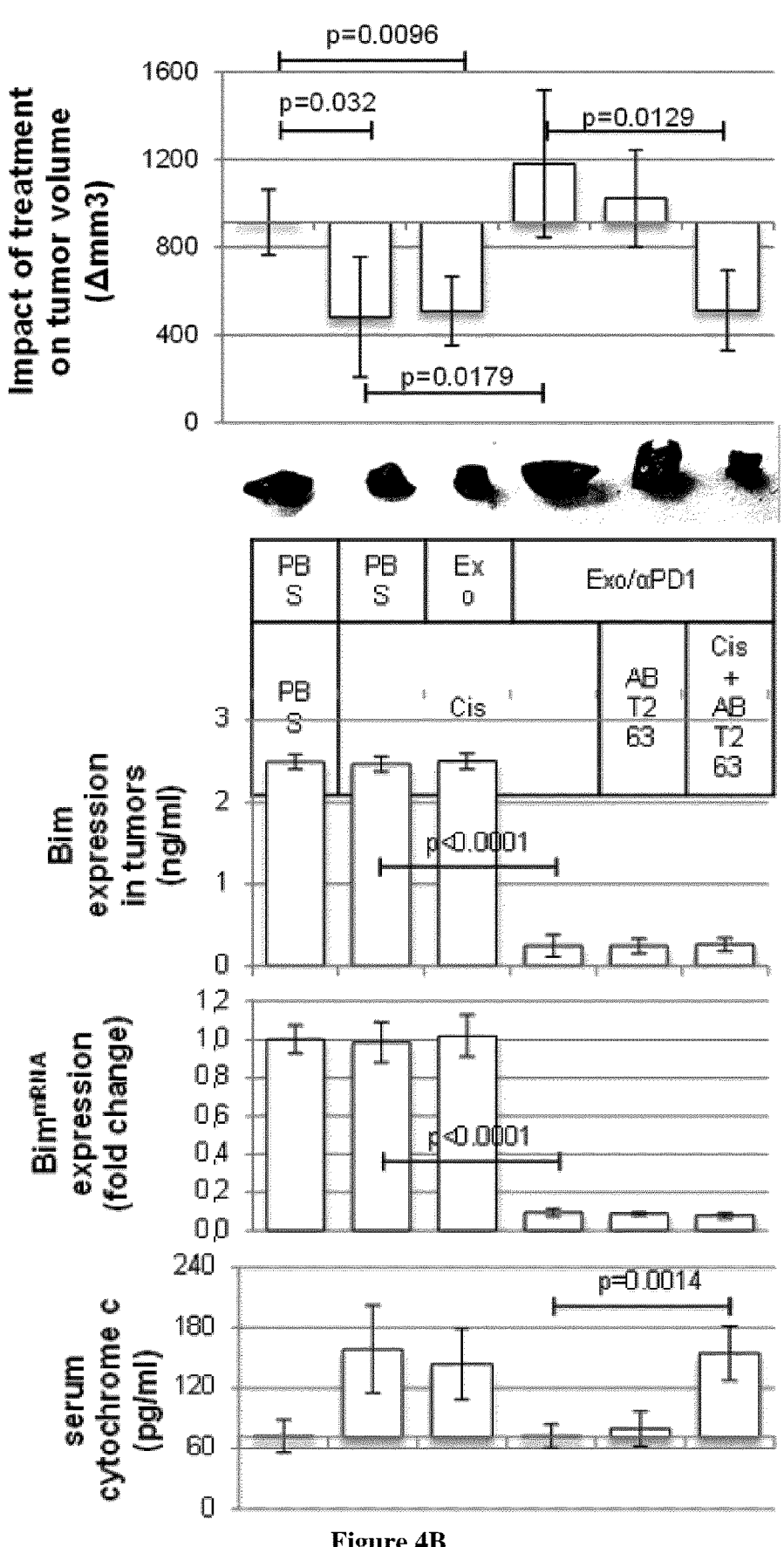

ABT263 efficacy was then assessed in A549-inoculated xenograft mice (data not shown). As expected, the CIS treatment decreased the volume of A549-induced tumors (FIG. 4B). The administration of Exo did not alter the effects of CIS on the A549 tumor, in contrast to the Exo/αPD1 inoculation which abrogated the anti-tumor activity of CIS. We also noted that the Exo/αPD1 inoculation decreased the Bim expression (at protein and mRNA levels) in tumors.

ABT263 induced similar activity and suppressed the deleterious effect of Exo/αPD1 on the CIS-resistance of cancer cells (FIG. 4B). Our results showed that ABT263 could be used to abrogate the Exo/αPD1-induced resistance to cisplatin treatment. In addition, we observed a significant inverse correlation between the impact of treatment on tumor and the serum cytochrome c level (r=−0.9566; p=0.0028) (data not shown).

CONCLUSION

Recent progress in the understanding of the molecular mechanisms that govern the phenomenon of anti-PD1 resistance have made it possible to identify several major causes of this phenomenon (14-15): evolution in the neoantigen landscape (16), the presence of JAK1/2 mutations (17), the presence of β-2-microglobulin mutations (18), and the limited acquisition of memory potential on CD8+Tcells (19-20). While the most recent articles have identified signatures associated with or explaining the molecular mechanisms that govern the phenomenon of anti-PD1 resistance, Bertrand et al. (2017) demonstrate that the TNFα blockade overcomes resistance to anti-PD1 in a mouse experimental melanoma model and suggested that using anti-PD1 and anti-TNF antibodies could be a therapeutic solution for limiting the process of anti-PD1 resistance (21). By identifying the T cell-derived ExomiR-4315expression/Bimdown-regulation axis as a "pan-cancer cascade" of events associated with the phenomenon of resistance to anti-PD1 therapy, our study completes the list of molecular mechanisms that govern this phenomenon. Our study is thus the first to incriminate a horizontal RNA transfer process in the transduction of the phenomenon of resistance to anti-PD1 therapy. In this horizontal RNA transfer (22), donor cells are the T cells exposed to anti-PD1 therapy, recipient T cells are tumor cells, the exosome is the vehicle of transfer, and miR-4315 is the transferred biological information.

Over the past decade, miR research in the cancer field has identified miR as biomarkers for diagnosis, prognosis and prediction of drug efficacy, as therapeutic agents, such as onco- or tumor suppressor miR (23-24). In this pleotropic literature, the one concerning miR-4315 appears poor. Nevertheless, miR-4315 has been identified as being up-regulated in cancerous tissue compared with non-cancerous breast tissue (25), deregulated in colorectal cancer (26) and up-regulated in primary lung adenocarcinoma tissue compared with non-cancerous tissue (27). Our work is thus the first to associate exomiR-4315 expression with a putative biomarker value for predicting the anti-cancer therapy efficacy of miR-4315.

The literature has already reported that Bim expression levels can be used to predict the response to anti-PD1 therapy in patients with metastatic melanoma (28-29). In these articles, it is mentioned that the measurement of Bim levels in CD8+ T cells represents a promossing low invasive strategy to predict the response to anti-PD-1 therapy. Our study strongly differs from these findings as 1) our data involve T cells and not only CD8+ T cells, 2) Bim regulation occurs in tumor cells and not in immune cells, and 3) our study involves intercellular communication between T cells and cancer cells and not only T cells. In addition, our study identifies exosomal miRNA-4315 as the molecular cause of the regulation of Bim expression, while no molecular cause was underline by Dronca and al. (2016) (29). Thus, our data are not redundant of the ones existing in the literature since they are focused on Bim in tumor cells and not on Bim in T cells.

Our article opens the possibility to detect (by monitoring the exomiR-4315 level) certain non-responding patients to the use of anti-PD-1 and combination of anti-PD-1 and chemotherapy.

REFERENCES

Throughout this application, various references describe the state of the art to which this invention pertains. The disclosures of these references are hereby incorporated by reference into the present disclosure.

1 Haanen J B A G, Robert C. Immune Checkpoint Inhibitors. Prog Tumor Res 2015; 42: 55-66.

2 Gomes B, Driessens G, Bartlett D, Cai D, Cauwenberghs S, Crosignani S et al. Characterization of the Selective Indoleamine 2,3-Dioxygenase-1 (IDO1) Catalytic Inhibitor EOS200271/PF-06840003 Supports IDO1 as a Critical Resistance Mechanism to PD-(L)1 Blockade Therapy. Mol Cancer Ther 2018; 17: 2530-2542.

3 Hu Z I, Hellmann M D, Wolchok J D, Vyas M, Shia J, Stadler Z K et al. Acquired resistance to immunotherapy in MMR-D pancreatic cancer. J Immunother Cancer 2018; 6: 127.

4 Bucktrout S L, Bluestone J A, Ramsdell F. Recent advances in immunotherapies: from infection and autoimmunity, to cancer, and back again. Genome Med 2018; 10: 79.

5 lorgulescu J B, Braun D, Oliveira G, Keskin D B, Wu C J. Acquired mechanisms of immune escape in cancer following immunotherapy. Genome Med 2018; 10: 87.

6 Topalian S L, Hodi F S, Brahmer J R, Gettinger S N, Smith D C, McDermott D F et al. Safety, activity, and immune correlates of anti-PD-1 antibody in cancer. N Engl J Med 2012; 366: 2443-2454.

7 Ribas A, Hamid O, Daud A, Hodi F S, Wolchok J D, Kefford R et al. Association of Pembrolizumab With Tumor Response and Survival Among Patients With Advanced Melanoma. JAMA 2016; 315: 1600-1609.

8 Gettinger S N, Wurtz A, Goldberg S B, Rimm D, Schalper K, Kaech S et al. Clinical Features and Management of Acquired Resistance to PD-1 Axis Inhibitors in 26 Patients With Advanced Non-Small Cell Lung Cancer. J Thorac Oncol Off Publ Int Assoc Study Lung Cancer 2018; 13: 831-839.

9 Chen W, Liu X, Lv M, Chen L, Zhao J, Zhong S et al. Exosomes from drug-resistant breast cancer cells transmit chemoresistance by a horizontal transfer of microRNAs. PloS One 2014; 9: e95240.

10 Zheng P, Chen L, Yuan X, Luo Q, Liu Y, Xie G et al. Exosomal transfer of tumor-associated macrophage-derived miR-21 confers cisplatin resistance in gastric cancer cells. J Exp Clin Cancer Res CR 2017; 36: 53.

11 Wei F, Ma C, Zhou T, Dong X, Luo Q, Geng L et al. Exosomes derived from gemcitabine-resistant cells transfer malignant phenotypic traits via delivery of miRNA-222-3p. Mol Cancer 2017; 16: 132.

12 Bhome R, Del Vecchio F, Lee G-H, Bullock M D, Primrose J N, Sayan A E et al. Exosomal microRNAs (exomiRs): Small molecules with a big role in cancer. Cancer Lett 2018; 420: 228-235.

13 Barczyk K, Kreuter M, Pryjma J, Booy E P, Maddika S, Ghavami S et al. Serum cytochrome c indicates in vivo apoptosis and can serve as a prognostic marker during cancer therapy. Int J Cancer 2005; 116: 167-173.

14 O'Donnell J S, Long G V, Scolyer R A, Teng M W L, Smyth M J. Resistance to PD1/PDL1 checkpoint inhibition. Cancer Treat Rev 2017; 52: 71-81.

15 Wang Q, Wu X. Primary and acquired resistance to PD-1/PD-L1 blockade in cancer treatment. Int Immunopharmacol 2017; 46: 210-219.

16 Anagnostou V, Smith K N, Forde P M, Niknafs N, Bhattacharya R, White J et al. Evolution of Neoantigen Landscape during Immune Checkpoint Blockade in Non-Small Cell Lung Cancer. Cancer Discov 2017; 7: 264-276.

17 Zaretsky J M, Garcia-Diaz A, Shin D S, Escuin-Ordinas H, Hugo W, Hu-Lieskovan S et al. Mutations Associated with Acquired Resistance to PD-1 Blockade in Melanoma. N Engl J Med 2016; 375: 819-829.

18 Restifo N P, Marincola F M, Kawakami Y, Taubenberger J, Yannelli J R, Rosenberg S A. Loss of functional beta 2-microglobulin in metastatic melanomas from five patients receiving immunotherapy. J Natl Cancer Inst 1996; 88: 100-108.

19 Wherry E J, Kurachi M. Molecular and cellular insights into T cell exhaustion. Nat Rev Immunol 2015; 15: 486-499.

20 Pauken K E, Sammons M A, Odorizzi P M, Manne S, Godec J, Khan O et al. Epigenetic stability of exhausted T cells limits durability of reinvigoration by PD-1 blockade. Science 2016; 354: 1160-1165.

21 Bertrand F, Montfort A, Marcheteau E, Imbert C, Gilhodes J, Filleron T et al. TNFα blockade overcomes resistance to anti-PD-1 in experimental melanoma. Nat Commun 2017; 8: 2256.

22 Ramachandran S, Palanisamy V. Horizontal transfer of RNAs: exosomes as mediators of intercellular communication. Wiley Interdiscip Rev RNA 2012; 3: 286-293.

23 Hayes J, Thygesen H, Tumilson C, Droop A, Boissinot M, Hughes T A et al. Prediction of clinical outcome in glioblastoma using a biologically relevant nine-microRNA signature. Mol Oncol 2015; 9: 704-714.

24 Zhou K, Liu M, Cao Y. New Insight into microRNA Functions in Cancer: Oncogene-microRNA-Tumor Suppressor Gene Network. Front Mol Biosci 2017; 4: 46.

25 Wu Q, Lu Z, Li H, Lu J, Guo L, Ge Q. Next-generation sequencing of microRNAs for breast cancer detection. J Biomed Biotechnol 2011; 2011: 597145.

26 Liang G, Li J, Sun B, Li S, LU L, Wang Y et al. Deep sequencing reveals complex mechanisms of microRNA deregulation in colorectal cancer. Int J Oncol 2014; 45: 603-610.

27 Kim J, Lim N J, Jang S-G, Kim H K, Lee G K. miR-592 and miR-552 can distinguish between primary lung adenocarcinoma and colorectal cancer metastases in the lung. Anticancer Res 2014; 34: 2297-2302.

28 Dronca R S, Mansfield A S, Park S S, Dong H. BCL-2-interacting mediator of cell death (Bim) is a novel biomarker for response to anti-PD-1 therapy in patients with advanced melanoma. Immunotherapy 2016; 8: 1351-1353.

29 Dronca R S, Liu X, Harrington S M, Chen L, Cao S, Kottschade L A et al. T cell Bim levels reflect responses to anti-PD-1 cancer therapy. JCI Insight 2016; 1. doi: 10.1172/jci.insight.86014.

30 Brahmer J R, Drake C G, Wollner I, Powderly J D, Picus J, Sharfman W H et al. Phase I study of single-agent anti-programmed death-1 (MDX-1106) in refractory solid tumors: safety, clinical activity, pharmacodynamics, and immunologic correlates. J Clin Oncol Off J Am Soc Clin Oncol 2010; 28: 3167-3175.

31 Shanda S, Noonan A M, Bekaii-Saab T S, O'Neil B H, Sehdev A, Shaib W L et al. A phase II study of pembrolizumab in combination with mFOLFOX6 for patients with advanced colorectal cancer. J Clin Oncol 2017; 35: 3541-3541.

32 Gadgeel S M, Stevenson J P, Langer C J, Gandhi L, Borghaei H, Patnaik A et al. Pembrolizumab and platinum-based chemotherapy as first-line therapy for advanced non-small-cell lung cancer: Phase 1 cohorts from the KEYNOTE-021 study. Lung Cancer Amst Neth 2018; 125: 273-281.

33 Black M, Barsoum I B, Truesdell P, Cotechini T, Macdonald-Goodfellow S K, Petroff M et al. Activation of the PD-1/PD-L1 immune checkpoint confers tumor cell chemoresistance associated with increased metastasis. Oncotarget 2016; 7: 10557-10567.

34 Sampson J H, Aldape K D, Archer G E, Coan A, Desjardins A, Friedman A H et al. Greater chemotherapy-induced lymphopenia enhances tumor-specific immune responses that eliminate EGFRvIII-expressing tumor cells in patients with glioblastoma. Neuro-Oncol 2011; 13: 324-333.

35 Ghiringhelli F, Larmonier N, Schmitt E, Parcellier A, Cathelin D, Garrido C et al. CD4+CD25+ regulatory T cells suppress tumor immunity but are sensitive to cyclophosphamide which allows immunotherapy of established tumors to be curative. Eur J Immunol 2004; 34: 336-344.

36 Alizadeh D, Trad M, Hanke N T, Larmonier C B, Janikashvili N, Bonnotte B et al. Doxorubicin eliminates myeloid-derived suppressor cells and enhances the efficacy of adoptive T-cell transfer in breast cancer. Cancer Res 2014; 74: 104-118.

37 Ock C-Y, Kim S, Keam B, Kim S, Ahn Y-O, Chung E-J et al. Changes in programmed death-ligand 1 expression during cisplatin treatment in patients with head and neck squamous cell carcinoma. Oncotarget 2017; 8: 97920-97927.

38 Tran L, Allen C T, Xiao R, Moore E, Davis R, Park S-J et al. Cisplatin Alters Antitumor Immunity and Synergizes with PD-1/PD-L1 Inhibition in Head and Neck Squamous Cell Carcinoma. Cancer Immunol Res 2017; 5: 1141-1151.

39 Lindell T J, Weinberg F, Morris P W, Roeder R G, Rutter W J. Specific inhibition of nuclear RNA polymerase II by alpha-amanitin. Science 1970; 170: 447-449.

The invention claimed is:

1. A method of identifying a patient having or at risk of having or developing a resistance to anti-PD-1 therapy and treating the patient, comprising
   i) determining the expression level of exosomal miRNA-4315 in a sample from said patient,
   ii) comparing said expression level with a predetermined reference value
   iii) determining that the expression level of the exosomal miRNA-4315 is less than the predetermined reference value; and
   iv) treating, with the anti-PD-1 therapy, the patient determined to have an expression level of the exosomal miRNA-4315 that is less than the predetermined reference value.

2. The method according to claim 1, wherein the anti-PD-1 therapy is nivolumab, pembrolizumab or cemiplimab.

3. The method according to claim 1, wherein the sample is blood, plasma, serum, T cell-derived exosomes or a cancer biopsy.

4. The method according to claim 1, wherein the patient receives simultaneously, separately or in a sequential manner a standard chemotherapy with the anti-PD-1 therapy.

5. The method according to claim 4, wherein the standard chemotherapy is oxaliplatin, cisplatin, temozolomide, cyclophosphamide, doxorubicin or paclitaxel.

6. A method of treating cancer in a patient in need thereof, comprising,
   determining an expression level of exosomal miRNA-4315 in a sample from said patient,
   comparing said expression level with a predetermined reference value,
   determining that the expression level of the exosomal miRNA-4315 is higher than the predetermined reference value, and
   treating, with a BH3 mimetic agent, the patient determined to have an expression level of the exosomal miRNA-4315 that is higher than the predetermined reference value.

7. The method of claim 6, wherein the patient is resistant to an anti-PD-1 therapy.

8. The method according to claim 6, wherein the BH3 mimetic agent is selected from the group consisting of: ABT-737, venetoclax (ABT-199) and navitoclax (ABT-263).

9. The method according to claim 1, wherein the cancer is a glioblastoma (GBM), a lung cancer, a breast cancer or an ovarian cancer.

10. The method according to claim 6, wherein the cancer is a glioblastoma (GBM), a lung cancer, a breast cancer or an ovarian cancer.

* * * * *